(12) United States Patent
Werner et al.

(10) Patent No.: US 8,083,399 B2
(45) Date of Patent: Dec. 27, 2011

(54) METHOD FOR FABRICATING THERMAL EFFECT STANDARDS

(75) Inventors: Greg Werner, Puyallup, WA (US); Paul Shelley, Lakewood, WA (US); Paul Vahey, Seatle, WA (US); Wes Quigley, Auburn, WA (US)

(73) Assignee: The Boeing Company, Chicago, IL (US)

( * ) Notice: Subject to any disclaimer, the term of this patent is extended or adjusted under 35 U.S.C. 154(b) by 819 days.

(21) Appl. No.: 12/164,022

(22) Filed: Jun. 28, 2008

(65) Prior Publication Data

US 2009/0323757 A1     Dec. 31, 2009

(51) Int. Cl.
*G01N 25/20* (2006.01)
(52) U.S. Cl. ......................................................... 374/43
(58) Field of Classification Search ................ 374/4, 45, 374/46, 49, 50, 51, 52, 53, 55, 57; 250/341.1, 250/341.6
See application file for complete search history.

(56) References Cited

U.S. PATENT DOCUMENTS

| 4,483,629 | A  | * | 11/1984 | Schwarz et al. | ................ | 374/57 |
| 5,209,569 | A  | * | 5/1993  | Fujiwara et al. | ................ | 374/55 |
| 6,623,159 | B2 | * | 9/2003  | Takahara et al. | ................ | 374/55 |
| 6,784,431 | B2 |   | 8/2004  | Shelley et al. | | |
| 6,794,651 | B2 |   | 9/2004  | Shelley et al. | | |
| 6,903,339 | B2 |   | 6/2005  | Shelley et al. | | |
| 6,906,327 | B2 |   | 6/2005  | Shelley et al. | | |
| 7,064,331 | B2 | * | 6/2006  | Rothenfusser et al. | .... | 250/341.6 |
| 7,115,869 | B2 |   | 10/2006 | Shelley et al. | | |
| 7,223,977 | B2 |   | 5/2007  | Shelley et al. | | |
| 2002/0167988 | A1 | * | 11/2002 | Zhu | ................ | 374/55 |
| 2007/0009009 | A1 | * | 1/2007 | Dziki | ................ | 374/45 |

* cited by examiner

*Primary Examiner* — G. Bradley Bennett
(74) *Attorney, Agent, or Firm* — Tung & Associates

(57) ABSTRACT

A method for fabricating thermal effect standards includes providing an oven, placing at least one temperature sensor at measurement location in the oven, operating the oven, monitoring a temperature output of the at least one temperature sensor, providing at least one composite material specimen, placing the at least one composite material specimen at the measurement location in the oven and heat treating the at least one composite material specimen as at least one thermal effect standard by operating the oven according to the temperature output of the at least one temperature sensor. A method of determining a physical property of a composite material is also disclosed.

19 Claims, 3 Drawing Sheets

METHOD FOR FABRICATING THERMAL EFFECT STANDARDS

CROSS REFERENCE TO RELATED APPLICATIONS

This application is related to co-pending U.S. patent application Ser. No. 12/164,025, and Ser. No. 12/164,026; and Ser. No. 12/164,023, and Ser. No. 12/164,017, all filed concurrently herewith on Jun. 28, 2008, each of which applications is incorporated by reference herein in its entirety.

FIELD OF THE INVENTION

The disclosure relates to standards for determining thermal effect in composite materials. More particularly, the disclosure relates to a method for fabricating thermal effect standards which are suitable for accurately assessing thermal effect in composite material.

BACKGROUND OF THE INVENTION

Resin-fiber composite materials are utilized in a variety of applications including the aerospace industry, for example. Structures which are constructed of resin-fiber composite materials may be exposed to heat, which may affect the composite materials in various ways. These heat-induced effects may include chemical degradation in which changes such as oxidation, material loss and the breaking and/or forming of chemical bonds occurs in the polymer chemical structure of the composite materials. Resin decomposition, charring and fiber decomposition of the composite materials may occur at increasing temperatures.

Repair or removal of heat-affected resin-fiber composite materials on a structure may involve first determining the degree of harmful heat effect to the composite substrate. Although determining the degree of heat effect to composite materials may be performed by visual inspection, heat effect to resin-fiber composite materials may not be visually apparent. Current methods of determining the presence and extent of heat effect in resin-fiber composite materials includes obtaining a series of infrared spectra of a series of heat-affected composite standards and making a thermal effect multivariate calibration model with the IR spectra and the thermal effect information from the standards. An infrared spectrum obtained from the composite material the heat effect of which is in question can then be predicted by the thermal effect model to determine the presence and assess the degree of thermal effect in the composite material.

Calibration of infrared sensors to residue strength in composite materials correlates the resin condition as read from the infrared spectra to the residual strength of the material which degrades as the resin degrades with progressively increasing temperatures. Therefore, the infrared spectroscopy sensors may be calibrated using time-controlled thermal soak standards which are obtained by exposing various composite material controls to various temperatures for a particular time period such as one hour, for example. One method of preparing the standards includes placing the standards in an oven which is calibrated periodically and monitored continuously. Thermal effect to composite materials often does NOT follow a linear course and indeed is usually a combination of overlapping degradation mechanisms in the composite resin material. Moreover, the calibration method may utilize the entire area of the oven cavity rather than the particular area in which the composite standard is confined during heating of the standard. In application, oven temperature readings may be off by 25 F. Therefore, temperature sensors with a calibrated meter may be used to read and verify correct oven temperatures +/−1 degree F. The oven temperature may be set high or low to achieve the CORRECT reading per the temperature sensors.

Therefore, a method of making thermal effect standards for composite materials which takes into account the total thermal experience of the composite standard in terms of both time and temperature is needed.

SUMMARY OF THE INVENTION

The disclosure is generally directed to a method for fabricating thermal effect standards. An illustrative embodiment of the method includes providing an oven, placing at least one temperature sensor at a measurement locations in the oven, operating the oven, monitoring the temperature output of the at least one temperature sensor, providing at least one composite material specimen, placing the at least one composite material specimen at the measurement location in the oven and heat treating the at least one composite material specimen as at least one thermal effect standard by operating the oven according to the temperature output of the at least one temperature sensor.

The disclosure is further generally directed to a method of determining a physical property of a composite material. An illustrative embodiment of the method includes providing a series of composite materials with increasing amounts of thermal effect, irradiating the composite materials with broad-spectrum infrared energy, detecting infrared energy reflected from the composite material, obtaining residual mechanical strength data for the thermal effect composite material, performing a multivariate calibration on the spectra of the infrared energy reflected from the composite materials, providing a calibration model of thermal effect using the residual strength of the thermal effect standards as the calibration parameter (Y-block data) for the model, and using the model to predict residual mechanical strength in composite materials in question that may have thermal effect.

BRIEF DESCRIPTION OF THE ILLUSTRATIONS

DETAILED DESCRIPTION

Figure 1:
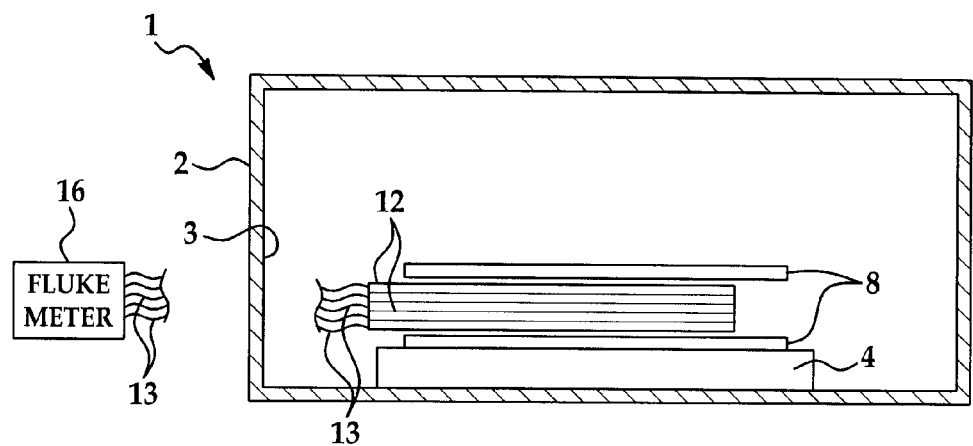
FIG. 1 is a cross-sectional schematic diagram of an oven with multiple temperature sensors placed in the oven to obtain temperature values for composite standards.
Figure 2:
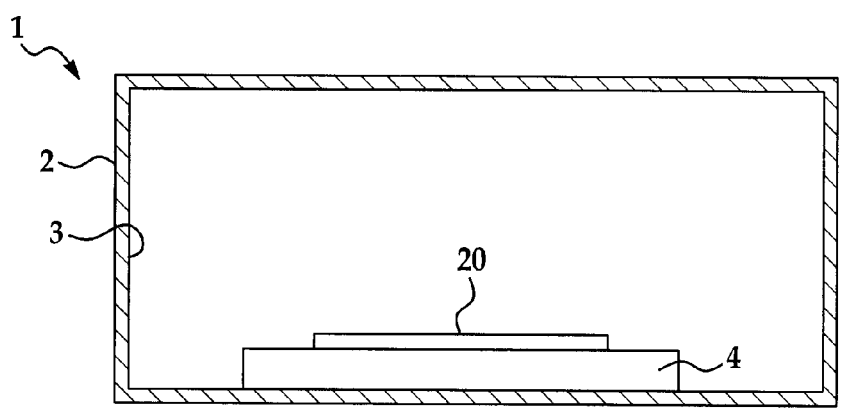
FIG. 2 is a cross-sectional schematic diagram of the oven, with a composite material specimen placed in the oven for heating in the fabrication of a composite material standard.
Figure 3:
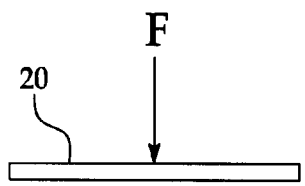
FIG. 3 is a side view of a heat-treated composite material standard subjected to a mechanical test force in obtaining values for residual strength.

Referring initially to FIGS. 1-4, an illustrative embodiment of a method of fabricating thermal effect standards is shown. As shown in block 402 of the flow diagram 400 in FIG. 4, an oven which is suitable for fabrication of thermal effect standards from composite material specimens is provided. As shown in FIG. 1, the oven 1 may include an oven wall 2 which defines an oven interior 3. A specimen support 4 may be provided in the oven interior 3. The oven 1 may be any conventional oven which is suitable for heating composite material specimens for the purpose of fabricating thermal effect standards and has 300 to 600 degree F. capability; therefore, various functional elements of the oven 1, such as heating elements, for example, are not shown in FIGS. 1 and 2 of the drawings.

In block 404 of the flow diagram 400, at least 5 temperature sensors, such as thermocouples, 12 are placed in the specimen oven 1 at a selected measurement location or locations in the oven interior 3, as shown in FIG. 1. In some applications, a bundle of temperature sensors 12 may be placed in the specimen oven 1 at the selected measurement locations in the oven interior 3. The temperature sensors 12 may be connected to a temperature sensor meter 16 such as through temperature sensor wiring 13, for example. The temperature sensor meter 16 may be adapted to monitor the temperature outputs of the temperature sensors 12 during operation of the specimen oven 1.

Figure 4:
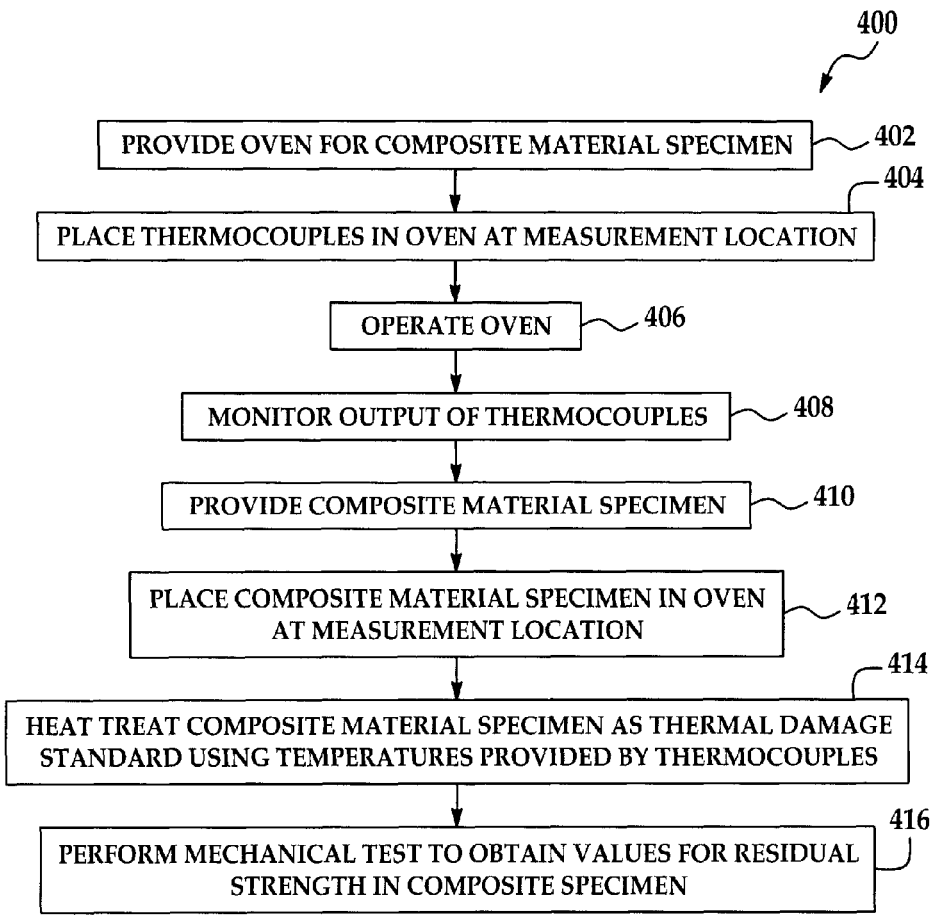
FIG. 4 is a flow diagram which illustrates an illustrative embodiment of a method of fabricating thermal effect standards.

In block 406 of FIG. 4, the specimen oven 1 is operated at predetermined exposure temperatures and exposure times which will subsequently be used to fabricate the thermal effect standards from the composite material specimens. As shown in block 408, the temperature outputs of the temperature sensors may be measured typically by the temperature sensor meter 16 (FIG. 1). The temperature control settings of the specimen oven 1 may be adjusted to facilitate heating of the measurement location in the specimen oven 1 to the predetermined temperatures as measured by the temperature sensors 12 and indicated by the temperature sensor meter 16. Therefore, the temperature sensors 12 provide precise temperature measurements of the measurement location in the specimen oven 1 which will correspond to the location at which heating of the composite material specimens will subsequently take place. The temperature control settings of the specimen oven 1 at the predetermined temperatures are noted or recorded to facilitate precision repeatability of the predetermined temperatures at the measurement location in the oven interior 3 for subsequent fabrication of the thermal effect standards. In some applications, the specimen oven 1 may be operated to heat the temperature sensors 12 to predetermined temperatures which lie along a calibration range for fabrication of the thermal effect standards. For example, the specimen oven 1 may be heated to predetermined temperatures of 350° F.; 325° F.; 375° F.; 400° F.; 425° F.; 450° F.; 475° F.; 500° F.; 525° F.; and 550° F. The oven may be pre-heated and temperature stabilized for 15 minutes to the treatment temperature before putting composite panels into the oven.

In block 410 of the flow diagram 400, at least one composite material specimen 20 (FIGS. 2 and 3) is provided. In block 412 of the flow diagram 400 and in FIG. 2, the composite material specimen 20 is placed at the measurement location in the oven interior 3. In block 414 of the flow diagram 400, the specimen oven 1 is operated to heat the composite material specimen 20 to the predetermined temperatures as measured by the temperature sensors 12 and indicated by the temperature sensor meter 16. The control settings of the specimen oven 1 are operated at the settings which were noted during operation of the specimen oven 1 at block 406, for a predetermined time period to fabricate the thermal control standards. Accordingly, the heat generated by the specimen oven 1 induces thermal effect in the composite material specimen 20. This thermal effect may include, for example, chemical degradation involving changes in the polymer chemical structure; oxidation, material loss and either breaking or forming of additional chemical links; and resin decomposition and charring and fiber decomposition. In some applications, successive composite material specimens 20 may be heated at temperatures which lie along a calibration range for fabrication of the thermal effect standards. For example, the composite material specimens 20 may be heated to predetermined temperatures of 350° F.; 325° F.; 375° F.; 400° F.; 425° F.; 450° F.; 475° F.; 500° F.; 525° F.; and 550° F., respectively. For each temperature setting the oven is preheated and temperature stabilized for 15 minutes before putting the composite panel into the oven. When the heated samples are removed from the oven a slow cooling process is recommended to prevent the samples from cracking and de-laminating.

The thermal effect which is induced in the composite material specimens 20 to form the thermal control standards may subsequently be used to determine the presence and extent of thermal effect in actual resin-fiber composite material samples. In block 416, the thermal control standards are subjected to mechanical forces (reference letter F in FIG. 3) in order to obtain values of residual strength in the standards. Typical mechanical tests that give good results for residual mechanical strength in composite material are un-notched compressions tests and interlaminar shear tests. The values of residual strength obtained for the thermal effect standards may be used to calibrate the infrared spectroscopy sensors (not shown) of an infrared testing device (not shown) to measurement of thermal effect in composite materials, which will be hereinafter described.

Figure 4A:
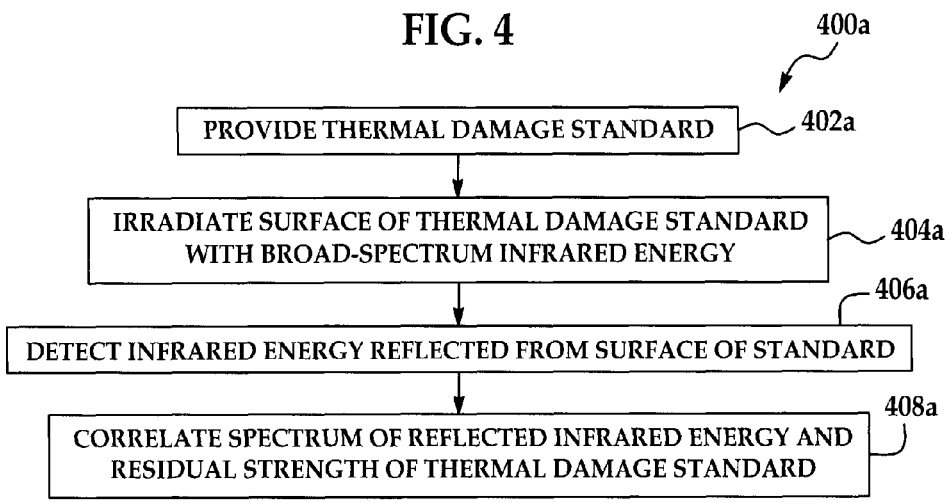
FIG. 4A is a flow diagram which illustrates an illustrative embodiment of a method of multivariate calibration for thermal effect in a series thermal effect standards with spectra of infrared energy reflected from the thermal effect standards.

Referring next to FIG. 4A, a flow diagram 400a which illustrates an illustrative embodiment of a method of multivariate calibration for thermal effect in a series of thermal effect standards with the spectra of infrared energy reflected from the thermal effect standards is shown. In block 402a, a series thermal effect standards is provided. The thermal effect standards may have been fabricated according to the method which was heretofore described with respect to the flow diagram 400 in FIG. 4. In block 404a, a surface of the thermal effect standard is irradiated with broad-spectrum infrared energy. In the range of 1.6 microns to 2.4 microns (near-IR) or 2.5 to 16.7 microns (mid-IR). In block 406a, infrared energy reflected from the surface of the thermal effect standards is detected. In block 408a, the spectra of the infrared energy which is reflected from the surface of the thermal effect standards is used with the residual strength of the thermal effect standards to create a multivariate calibration model for the residual strength of the thermal effect standards.

Figure 5:
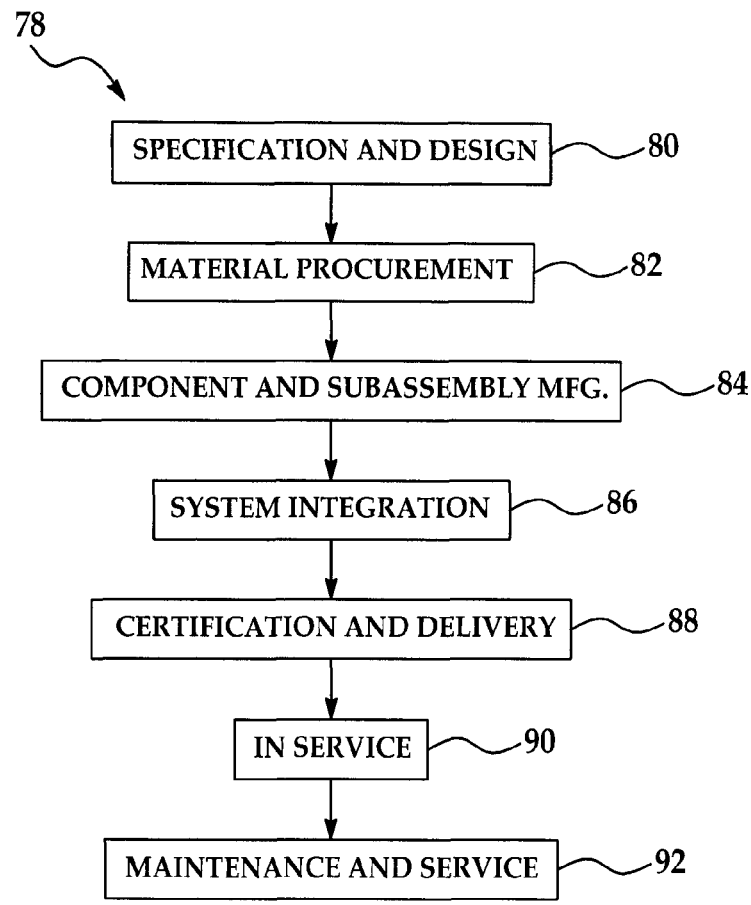
FIG. 5 is a flow diagram of an aircraft production and service methodology.
Figure 6:
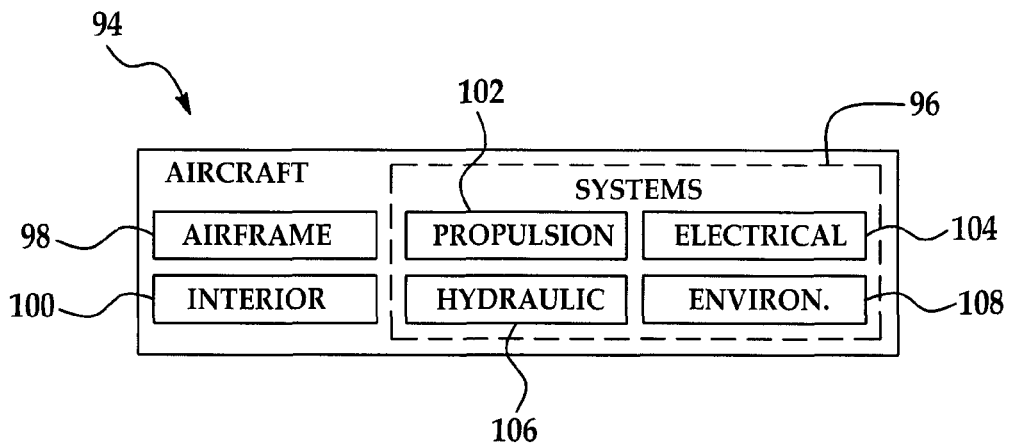
FIG. 6 is a block diagram of an aircraft.

Referring next to FIGS. 5 and 6, embodiments of the disclosure may be used in the context of an aircraft manufacturing and service method 78 as shown in FIG. 5 and an aircraft 94 as shown in FIG. 6. During pre-production, exemplary method 78 may include specification and design 80 of the aircraft 94 and material procurement 82. During production, component and subassembly manufacturing 84 and system integration 86 of the aircraft 94 takes place. Thereafter, the aircraft 94 may go through certification and delivery 88 in order to be placed in service 90. While in service by a customer, the aircraft 94 may be scheduled for routine maintenance and service 92 (which may also include modification, reconfiguration, refurbishment, and so on).

Each of the processes of method 78 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 6, the aircraft 94 produced by exemplary method 78 may include an airframe 98 with a plurality of systems 96 and an interior 100. Examples of high-level systems 96 include one or more of a propulsion system 102, an electrical system 104, a hydraulic system 106, and an environmental system 108. Any number of other systems may be included. Although an aerospace example is shown, the principles of the invention may be applied to other industries, such as the automotive industry.

The apparatus embodied herein may be employed during any one or more of the stages of the production and service method 78. For example, components or subassemblies corresponding to production process 84 may be fabricated or manufactured in a manner similar to components or subassemblies produced while the aircraft 94 is in service. Also, one or more apparatus embodiments may be utilized during the production stages 84 and 86, for example, by substantially expediting assembly of or reducing the cost of an aircraft 94. Similarly, one or more apparatus embodiments may be utilized while the aircraft 94 is in service, for example and without limitation, to maintenance and service 92.

Although the embodiments of this disclosure have been described with respect to certain exemplary embodiments, it is to be understood that the specific embodiments are for purposes of illustration and not limitation, as other variations will occur to those of skill in the art.

What is claimed is:

1. A method for fabricating a thermal effect standard for subsequent calibration of broad-spectrum IR Spectroscopy measurements used to predict a residual strength of a composite material, comprising:
    providing an oven;
    placing at least one temperature sensor at a measurement location in said oven;
    operating said oven;
    monitoring a temperature output of said at least one temperature sensor;
    providing at least one composite material specimen;
    placing said at least one composite material specimen at said measurement location in said oven;
    heat treating said at least one composite material specimen as at least one thermal effect standard by operating said oven according to said temperature output of said at least one temperature sensor; and
    obtaining values for residual strength in said at least one thermal effect standard by subjecting said at least one thermal effect standard to a mechanical test.

2. The method of claim 1 further comprising pre-heating and stabilizing a temperature of said oven prior to said placing said at least one composite material specimen at said measurement location in said oven.

3. The method of claim 2 wherein said pre-heating and stabilizing a temperature of said oven comprises pre-heating said oven for about 15 minutes.

4. The method of claim 1 wherein said placing at least one temperature sensor at a measurement location in said oven comprises placing a plurality of bundled temperature sensors at said measurement location in said oven.

5. The method of claim 1 wherein said monitoring a temperature output of said at least one temperature sensor comprises providing a temperature sensor meter, connecting said temperature sensor meter to said at least one temperature sensor and indicating said temperature output of said at least one temperature sensor on said temperature sensor meter.

6. The method of claim 1 wherein said placing said at least one composite material specimen at said measurement Location in said oven comprises placing a plurality of successive composite material specimens at said measurement location in said oven and wherein heat treating said at least one composite material specimen as at least one thermal effect standard comprises heat treating said plurality of successive composite material specimens as a plurality of thermal effect standards, respectively, at a plurality of temperature outputs of said at least one temperature sensor.

7. The method of claim 6 wherein said heat treating said plurality of successive composite material specimens as a plurality of thermal effect standards at a plurality of temperature outputs of said at least one temperature sensor comprises heat treating said plurality of successive composite material specimens at temperatures of 350° F., 325° F., 375° F., 400° F., 425° F., 450° F., 475° F., 500° F., 525° F. and 550° F., respectively.

8. A method for fabricating and using a thermal effect standard for calibration of broad-spectrum IR Spectroscopy measurements to predict a residual strength of composite material, comprising:
    providing an oven;
    placing a plurality of temperature sensors at a measurement location in said oven;
    operating said oven;
    monitoring a temperature output of said plurality of temperature sensors;
    providing at least one composite material specimen;
    placing said at least one composite material specimen at said measurement location in said oven;
    heat treating said at least one composite material specimen as at least one thermal effect standard by operating said oven according to said temperature output of said plurality of temperature sensors;
    irradiating a surface of said at least one thermal effect standard with broad-spectrum infrared energy;
    detecting infrared energy reflected from said at least one thermal effect standard; and
    correlating a spectrum of said infrared energy reflected from said at least one thermal effect standard and a residual strength of said at least one thermal effect standard, said correlation used to predict a residual strength of a composite material subjected to a second broad-spectrum IR Spectroscopy measurement.

9. The method of claim 8 wherein said correlating a spectrum of said infrared energy reflected from said at least one thermal effect standard and a residual strength of said at least one thermal effect standard comprises obtaining values for said residual strength of said at least one thermal effect standard by subjecting said at least one thermal effect standard to a mechanical test.

10. The method of claim 8 further comprising pre-heating and stabilizing a temperature of said oven prior to said placing said at least one composite material specimen at said measurement location in said oven.

11. The method of claim 10 wherein said pre-heating and stabilizing a temperature of said oven comprises pre-heating said oven for about 15 minutes.

12. The method of claim 8 wherein said placing a plurality of temperature sensors at a measurement location in said oven comprises placing a plurality of bundled temperature sensors at said measurement location in said oven.

13. The method of claim 8 wherein said monitoring a temperature output of said plurality of temperature sensors comprises providing a temperature sensor meter, connecting said temperature sensor meter to said plurality of temperature sensors and indicating said temperature output of said plurality of temperature sensors on said temperature sensor meter.

14. The method of claim 8 wherein said placing said at least one composite material specimen at said measurement location in said oven comprises placing a plurality of successive composite material specimens at said measurement location in said oven and wherein heat treating said at least one composite material specimen as at least one thermal effect standard comprises heat treating said plurality of successive composite material specimens as a plurality of thermal effect standards, respectively, at a plurality of temperature outputs of said plurality of temperature sensors.

15. The method of claim 14 wherein said heat treating said plurality of successive composite material specimens as a plurality of thermal effect standards, respectively, at a plurality of temperature outputs of said plurality of temperature sensors comprises heat treating said plurality of successive composite material specimens at temperatures of 350° F., 325° F., 375° F., 400° F., 425° F., 450° F., 475° F., 500° F., 525° F. and 550° F., respectively.

16. A method of determining a physical property of a composite material, comprising:
providing a composite material;
irradiating said composite material with broad-spectrum infrared energy;
detecting infrared energy reflected from said composite material;
performing multivariate analysis on a spectrum of said infrared energy reflected from said composite material;
providing at least one thermal effect standard;
obtaining a correlation of a spectrum of infrared energy reflected from said at least one thermal effect standard and a residual strength of said at least one thermal effect standard; and
quantifying a degree of heat effect including predicting a residual strength of said composite material by comparing results of said multivariate analysis with said correlation.

17. The method of claim 16 wherein said providing at least one thermal effect standard comprises:
providing an oven;
placing a plurality of temperature sensors at a measurement location in said oven;
operating said oven;
monitoring a temperature output of said plurality of temperature sensors;
providing at least one composite material specimen;
placing said at least one composite material specimen at said measurement location in said oven; and
heat treating said at least one composite material specimen as at least one thermal effect standard by operating said oven according to said temperature output of said plurality of temperature sensors.

18. The method of claim 17 further comprising obtaining values for said residual strength in said at least one thermal effect standard by subjecting said at least one thermal effect standard to a mechanical test.

19. The method of claim 17 further comprising placing metal plates at said measurement location in said oven and wherein said placing plurality of temperature sensors at a measurement location in said oven comprises placing a bundle of temperature sensors between said metal plates.

* * * * *